United States Patent [19]

Sibley et al.

[11] 4,104,187

[45] Aug. 1, 1978

[54] COMPOSITION AND METHOD TREATING SOFT CONTACT LENSES AT ELEVATED TEMPERATURES

[75] Inventors: Murray J. Sibley, Berkeley; Gordon H. K. Yung, Sunnyvale; Petronio D. Urrea, Sunol, all of Calif.

[73] Assignee: Barnes-Hind Pharmaceuticals, Inc., Sunnyvale, Calif.

[21] Appl. No.: 676,280

[22] Filed: Apr. 12, 1976

[51] Int. Cl.$^2$ .......................... C11D 1/84; C11D 1/48
[52] U.S. Cl. .................................. 252/106; 252/542; 252/546; 252/547; 134/2; 134/40; 134/42
[58] Field of Search .............................. 21/2, 56–58; 134/35, 40, 42; 252/106, 542, 546, 548; 424/78, 80, 81, 316, 326, 339

[56] References Cited

U.S. PATENT DOCUMENTS

| 2,089,212 | 4/1937 | Kritchevsky | 260/404 |
|---|---|---|---|
| 3,171,752 | 3/1965 | Rankin | 106/194 |
| 3,882,036 | 5/1975 | Krezanoski et al. | 252/106 |
| 3,888,782 | 6/1975 | Boghosian et al. | 252/106 |
| 3,908,680 | 9/1975 | Krezanoski | 134/27 |
| 4,013,576 | 3/1977 | Loshaek | 252/106 |
| 4,046,706 | 9/1972 | Krezanoski | 252/106 |

FOREIGN PATENT DOCUMENTS

1,076,331  2/1960  Fed. Rep. of Germany.
1,231,541  5/1971  United Kingdom.

OTHER PUBLICATIONS

Sanders et al., Soap & Chemical Specialties, "High Activity Alkanolamide Detergents," Jan. 1956, pp. 33, 34, 35, 36, 57.

Mannheimer, H. S., Soap & Chemical Specialties, "Amphoteric Surfactants," Sep. 1958, pp. 56–58, 206.

*Primary Examiner*—P.E. Willis, Jr.
*Attorney, Agent, or Firm*—Townsend and Townsend

[57] ABSTRACT

Method and compositions are provided for elevated temperature disinfection of soft contact lenses. The lenses are heated at a temperature and for a time sufficient to provide disinfection in an aqueous stabilized saline solution having a small amount of a non-eye-irritating neutral surfactant. Particularly effective are N-hydroxyalkylated fatty acid amides.

5 Claims, No Drawings

COMPOSITION AND METHOD TREATING SOFT CONTACT LENSES AT ELEVATED TEMPERATURES

BACKGROUND OF THE INVENTION

1. Field of the Invention

A commonly used method for disinfection of soft contact lenses is to introduce the soft contact lens into a small holder containing a stabilized aqueous saline solution. The holder is introduced into a heater, where the holder and its contents are heated either by boiling water or a closed heated air environment. Temperatures of the solution in the holder generally range from about 70°–90° C and times for which the holder contents are maintained in this temperature range will generally vary from about 10–20 minutes. After cooling, the lenses may be removed from the holder, desirably rinsed and may then be introduced into the eye or left soaking, so as to remain hydrated over night.

While the disinfection method using an elevated temperature, frequently referred to as "boiling", is effective for disinfection, it has created a number of serious porblems for the soft contact lens wearer. Because of the chemical nature of the soft contact lens, a wide variety of materials will tenaciously adhere to the contact lens. Of particular importance are proteinaceous materials and lipid materials. The thermal treatment of the lens results in denaturation of the protein, which then forms a strongly adhering layer to the lens. Repetitive thermal disinfection of the contact lenses results in a continuous buildup of the proteinaceous layer, which also results in the binding of other materials, such as lipids, dust particles, and the like. As the proteinaceous layer builds up, the lens becomes irritating to the eye and with continued buildup loses its optical quality and clarity.

Any attempt to prevent the formation and buildup of a tenaciously adhering proteinacous layer during thermal disinfection is limited by a number of considerations. Among these considerations is the fact that the lens may be taken from the boiling solution and placed directly in the eye. Therefore, the solution must not introduce materials into the lens which will be irritating to the eye. Also, it is convenient that the boiling solution also be a rinse and soak solution, so that the lens after boiling may be rinsed with the same solution or be stored in the solution until used. Any additives introduced into the boiling solution must be stable and should not interact detrimentally with the contact lens. As a practical matter, the boiling solution must be stable and have a long shelf life, must be clear and must not adversely affect the optical characteristics and quality of the lens.

2. Description of the Prior Art

Reference is made to Applicant's copending application Ser. No. 651,744, filed Jan. 23, 1976.

SUMMARY OF THE INVENTION

Method and compositions are provided for removing tenaciously adhering denatured protein deposits from soft contact lenses or preventing the buildup of proteinaceous deposits during normal elevated temperature disinfection. Including in the aqueous saline "boiling" solution employed for disinfection is a small but sufficient non-eye-irritating amount of a neutral surfactant e.g. nonionic or ampholytic, particularly N-hydroxyalkylated carboxamides. The concentration of the surfactant will be less than 0.5w/v, usually less than 0.1w/v and preferably from about 0.001 to 0.05w/v.

DESCRIPTION OF THE SPECIFIC EMBODIMENTS

The subject invention is concerned with prolonging the useful lifetime of soft contact lenses by a simple and efficient technique which does not further complicate procedures employed by the wearer in the use of soft contact lenses. Soft contact lenses by virtue of their polar-non-polar character are subject to the accumulation of a large variety of materials, particularly proteinaceous materials and lipid materials in the eye, dust as well as other materials from the air, handling and cosmetics. These materials coat and adhere to the lens. Present disinfecting procedures employ immersing the soft contact lens in an aqueous saline medium in a closed container and heating the aqueous saline medium to a temperature of at least about 70° C for a time sufficient to provide disinfection, usually from about 10–20 minutes. The heat may be transmitted to the container either by steam or dry air. It is believed, that further studies may establish that temperatures as low as 60° C may be employed effectively, although the time may be further extended.

The result of heating the soft contact lens with the soilant coating is to denature the proteins present so as to form a strongly adhering coating which serves as a base for additional layers of soilant to adhere to. After a relatively short time, a coating can build up which interferes with the optical clarity and quality of the soft contact lens.

In accordance with this invention, the buildup of soilant on soft contact lens is prevented and denatured protein containing soilant coatings are removed by including in the aqueous saline solution during the disinfection procedure a small but sufficient amount of a non-eye-irritating neutral surfactant i.e. non-ionic surfactants and ampholytic surfactants.

The soft contact lens is removed from the eye and introduced into a container having a solution according to the subject invention in an amount sufficient to completely immerse the soft contact lens. The container is then closed and introduced into a heating device, which heats the solution to a temperature presently at or in excess of 70° C for a time usually equal to or exceeding 10 minutes and generally not exceeding 30 minutes. The container is then allowed to cool and the lens removed and preferably rinsed, although it may be put immediately into the eye. By rinsing is intended putting a few drops of a solution according to this invention on the lens and manually rubbing the lens with the fingers to ensure uniform distribution of the solution over the lens' surface. The lens may then be introduced into the eye. Alternatively the lens may be stored in the solution until removed for use, so that it remains in a sterile and hydrated form during storage.

Soft contact lenses are normally comprised of a cross-linked polymer of hydroxyethyl methacrylate, either homopolymerized or co-polymerized with vinyl pyrrolidone, either as a random or block co-polymer. Alternatively, silicone lenses may also be employed in the subject invention, where the silicone lenses are normally derived from dimethyl polysiloxane, usually modified by substituting a number of the methyl groups with another group, e.g. phenyl.

BOILING SOLUTION COMPONENTS

The solutions of the subject invention are aqueous saline solutions buffered to a physiological pH and having a preservative system and a small but sufficient amount of a neutral surfactant.

The first component to be considered is the neutral surfactant. What is intended by neutral is that a substantial amount of the surfactant, normally greater than 40 mole percent, has no total charge at the pH employed. The neutral surfactants are non-ionic surfactants and ampholytic surfactants.

The surfactants which are employed must be completely miscible with water at the concentrations employed and must provide a clear solution. In addition, the surfactant must be stable under the disinfecting conditions, must not act adversely with the soft contact lens, nor with other materials present in the solution and, finally, must not irritate the eye. Therefore, the surfactant must not be adsorbed by the soft contact lens, while being capable of solubilizing the proteinaceous and lipid materials adsorbed on the lens and preventing redeposition during the disinfection treatment and subsequent storage.

The first group of surfactants are the non-ionic surfactants, particularly hydroxyalkylated surfactants and polyoxyalkylated surfactants. Extremely effective at very low concentrations are N-hydroxyalkylated carboxamides of fatty acids of from 10-18 carbon atoms, preferably of from 12-14 carbon atoms and having from 0-1 site of olefinic unsaturation as the only unsaturation, preferably saturated. There will normally be two hydroxyalkyl groups of from 2-3 carbon atoms, which may be the same or different.

The polyoxyalkylated non-ionic detergents may be solely polyoxyalkylene groups of from 2-3 carbon atoms or may have a polyoxyalkylene chain bonded directly or indirectly to an aliphatic chain of from 10-18 carbon atoms. The alkyl containing group may be a sorbitan ester, an alkylphenyl, alkyl, a carboxylic acid, or the like. The polyoxyalkylene chain may be a homo-oligomer or co-oligomer, with the homo-oligomer normally being ethyleneoxy groups and the co-oligomer being a random or block co-oligomer of ethyleneoxy and propyleneoxy groups. These various non-ionic detergents are commercially available under a wide variety of trade names, such as Tween, Igepal, Pluronic, Brij, and Myrj. The alkylene oxy chains will generally range on the average from about 5 to 60 oxyalkylene units.

The ampholytic detergents will normally be betaines having an aliphatic carbon chain bonded to nitrogen of from about 10-18 carbon atoms, preferably from about 10-14 carbon atoms. Of particular interest are compounds of the following formula

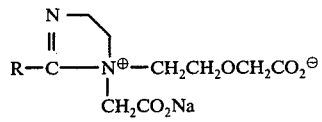

wherein R is of from 19-13 carbon atoms, usually 11 carbon atoms.

Individual surfactants or combinations of surfactants may be employed with the total concentration being in the indicated range. As indicated previously, the concentration of the surfactant will be less than 0.5w/v, generally ranging from about 0.001-0.1w/v, preferably from about 0.001-0.05w/v. (w/v intends grams per 100ml).

The solution employed is a saline solution having from about 0.3-1.5 weight percent, usually 0.85 to 0.95 weight percent sodium chloride, normally isotonic.

Ophthamologically acceptable buffers will be employed to achieve the desired pH, generally in the range of 5-9, preferably from about 6.5-7.6, and particularly preferred from about 7-7.4. Illustrative buffers include borate, phosphate, citrate, carbonate and lactate, although other physiologically acceptable buffers may be employed. The buffer concentration will generally be from about 0.05 to 0.5 weight percent, normally being about 0.1 weight percent.

A preservative system will also be included in the solution, which serves to maintain the solution sterile. Of particular interest are Thimerosal, the sodium salt of ethylene diamine tetraacetic acid (EDTA), sorbic acid, and methyl- and propyl-paraben. Depending upon the particular preservative system employed, which will frequently involve combinations of materials, the individual materials will generally be present in from about 0.001-0.1 weight percent, although higher concentrations may be used without significant advantage.

EXPERIMENTAL

In order to demonstrate the effectiveness of the subject invention, soft contact lenses were dipped in egg white, allowed to drain, and either introduced in a conventional commercial boiling solution or in a solution according to this invention. The conventional boiling solution is an aqueous isotonic saline solution employing a borate buffer at about 0.1w/v and having Thimerosal and EDTA as preservatives at about 0.001 weight percent. The lens was then introduced into a lens container containing the commercial boiling solution, the lens container closed and the container introduced into a conventional disinfecting heater employing water as the heat source. The heater provides approximately a 90° C temperature in the container for about 10-15 minutes. This process was repeated twenty times with 12 lenses, by which time there was a noticeable buildup of proteinaceous material.

In accordance with the Bausch and Lomb scale of I-IV, the lenses would be rated at III. (The Bausch and Lomb scale is set as follows: no soilant is present or soilant can only be seen with magnification after the lens is blotted dry I; soilant can be seen without magnification after the lens is blotted dry-II; soilant can be seen with the lens wet with the aid of light or magnification-III; soilant can be seen with the lens wet by the naked eye-IV.) Approximately 15-20% of the lens surface area was found to be covered with a strongly adhering coat. The lenses were then tested by employing a disinfecting cycle with the same solution to which varying concentrations of the lauramide of di(hydroxyethyl)amine was added. The specific concentrations were about 0.001, 0.005, 0.01 and 0.1 weight percent. In each case, the lenses were cleaned so that there was no apparent coating remaining and the lenses were rated I. When 0.1 weight percent of 2-undecyl-3-(2'-carboxymethoxyethyl)-3-carboxymethyl-1-imidazoline disodio salt hydroxide was added to a conventional "boiling" solution, and the lens subjected to the disinfecting treatment, the lens was completely freed of the proteinaceous soilant. When the same disinfecting cycle ws used, accept that 0.001 weight percent and 0.01 weight percent concentrations of the above lauramide were employed in the boiling solution, after 20 cycles, there was no observable formation of a soilant film on the soft contact lenses.

The subject invention provides a convenient way for greatly extending the useful lifetime of soft contact lenses, while retaining the optical clarity and quality of the lenses. By use of a small but sufficient amount of a neutral detergent in a thermal disinfecting solution, the accumulation of soilants on the lenses is prevented without requiring additional steps from those presently used for the maintenance of soft contact lenses. Not only is the surfactant solution capable of maintaining the lenses for long periods of time with their original clarity and quality, but it is also effective in removing soilants which have built up over a period of time. In addition, the surfactants do not irritate the eye, so that the lens may be introduced directly into the eye after being subject to the disinfection treatment. The surfactants also aid in the disinfecting capability of the thermal treatment.

Although the foregoing invention has been described in some detail by way of illustration and example for purposes of clarity of understanding, it will be obvious that certain changes and modifications may be practiced within the scope of the appended claims.

What is claimed is:

1. A soft lens thermal disinfecting and cleaning solution consisting essentially of:

an aqueous isotonic saline solution buffered with a physiologically acceptable buffer at a pH in the range of about 6.5–7.6, having a physiologically acceptable preservative system comprising at least one member of the group consisting of ethyl(2-mercaptobenzato-S) mercury sodium salt, ethylene diamine tetraacetic acid and sorbic acid, and from 0.001–0.1w/v of a fatty acid amide of 10 to 18 carbon atoms of diethanolamine.

2. A soft lens thermal disinfecting and cleaning solution according to claim 1, wherein said fatty acid amide of diethanolamine is the lauramide of diethanolamine.

3. A method for disinfecting and cleaning soft contact lenses which comprises heating said lenses in a solution at a temperature of at least 60° C for a time sufficient to disinfect and clean such soft contact lens, said solution consisting essentially of:

an aqueous saline solution buffered with a physiologically acceptable buffer to a pH in the range of 6.5–7.6 having a physiologically acceptable perservative system comprising at least one member of the group consisting of ehtyl(2-mercaptobenzato-S)mercury sodium salt, ethylene diamine tetraacetic acid and sorbic acid in a total amount of from about 0.001 to 0.1 weight percent and from about 0.001–0.1w/v of a non-eye irritating neutral surfactant selected from the group consisting of fatty acid amides of from 10 to 18 carbon atoms of diethanolamine and 2-undecyl-3-(2'-carboxymethoxyethyl)-3-carboxymethyl-1-imidazoline disodio salt hydroxide.

4. A method according to claim 3, wherein said surfactant is the lauramide of diethanolamine.

5. A method according to claim 3, wherein said surfactant is 2-undecyl-3-(2'-carboxymethoxyethyl)-3-carboxymethyl-1-imidazoline disodio salt hydroxide.

* * * * *